United States Patent

Koehl et al.

[11] Patent Number: 6,100,437
[45] Date of Patent: Aug. 8, 2000

[54] ALKYLATION PROCESS OF ALKYL-BENZENE WITH OLEFIN USING A SODIUM-AND-POTASSIUM CATALYST

[75] Inventors: David J. Koehl, Orangeburg; Edward A. Burt, Lexington, both of S.C.; Patrick T. Ward, Austin, Tex.

[73] Assignee: Albemarle Corporation, Richmond, Va.

[21] Appl. No.: 09/113,650

[22] Filed: Jul. 10, 1998

[51] Int. Cl.[7] .......................... C07C 2/64; C07C 15/067; C07C 2/66
[52] U.S. Cl. ............................................. 585/452; 585/457
[58] Field of Search ..................... 585/457, 452

[56] References Cited

U.S. PATENT DOCUMENTS

| | | | |
|---|---|---|---|
| 2,728,802 | 12/1955 | Closson | 260/668 |
| 2,750,384 | 6/1956 | Closson | 260/290 |
| 2,769,850 | 11/1956 | Closson | 260/668 |
| 4,179,580 | 12/1979 | Cobb | 546/349 |
| 4,731,196 | 3/1988 | Staton et al. | 252/184 |
| 4,914,250 | 4/1990 | Smith | 585/452 |
| 4,929,783 | 5/1990 | Smith | 585/452 |
| 4,950,831 | 8/1990 | Staton et al. | 585/447 |
| 4,952,546 | 8/1990 | Knuuttila et al. | 502/174 |
| 4,977,124 | 12/1990 | Smith | 502/174 |
| 4,982,035 | 1/1991 | Smith | 585/452 |
| 5,104,843 | 4/1992 | Staton et al. | 502/174 |
| 5,157,186 | 10/1992 | Staton et al. | 585/467 |
| 5,252,345 | 10/1993 | Hu et al. | 424/684 |

OTHER PUBLICATIONS

Schramm et al., "The Alkali Metal Catalyzed Alkylation of Toluene with Propylene", Journal of Am. Chem. Soc., 1960, vol. 82, pp. 4912–4918.

Herman Pines and Wayne Stalick, Academic Press, Base-Catalyzed Reactions of Hydrocarbons and Related Compounds, 1977, pp. 240–308.

*Primary Examiner*—Walter D. Griffin
*Assistant Examiner*—Thuan D. Dang
*Attorney, Agent, or Firm*—Philip M. Pippenger

[57] ABSTRACT

An alkylbenzene is alkylated with an alkene, in the presence of a sodium/potassium alloy catalyst, on a saturated carbon atom which is alpha to the ring at temperatures which are lower than the temperatures used in a current commercial process. In a pre-alkylation reaction, the catalyst is reacted with a compound which has a saturated carbon atom alpha to a double bond in order to form a catalytic species. Higher amounts of catalyst are used in the pre-alkylation reaction than in the analogous reaction of the current commercial process. Following alkylation, the phase which contains the alkylation product is separated from the phase which contains the catalytic species. The process produces less isomeric and other soluble byproducts, and enables the efficacious production of longer chain alkylbenzenes without the formation of insoluble tars characteristic of the current commercial process.

31 Claims, No Drawings

ALKYLATION PROCESS OF ALKYL-BENZENE WITH OLEFIN USING A SODIUM-AND-POTASSIUM CATALYST

TECHNICAL FIELD

This invention relates to a novel, highly efficient method for the production of alkylbenzene compounds.

BACKGROUND

Alkylbenzenes are useful, for example, as intermediates in the production of various end products. As an embodiment of this invention, among the products which can be synthesized more efficiently using alkylbenzenes prepared in accordance with this invention are members of the family of compounds which comprise the 2-aryl propionic acid derivatives. Specifically, ibuprofen, a commercially successful, over-the-counter, analgesic can be synthesized using isobutyl benzene prepared as a raw material.

It has been known for decades that alkali metals, when reacted with alkylbenzenes, will displace benzylic hydrogens. The resulting alkylbenzene anion/alkali metal cation pair will undergo a reaction with olefins at certain temperatures to give alkylation products in which some or all saturated benzylic carbon atoms are alkylated in such a way as to replace some or all of the benzylic hydrogen atoms on a carbon atom with one aliphatic chain per benzylic hydrogen atom. Such reactions can yield a variety of products, depending on the number of saturated benzylic carbon atoms and the number of hydrogen atoms on a given benzylic carbon atom. In the commercial production of alkylbenzenes, a product of high purity is generally desired, and byproducts must be removed.

An especially serious problem with the present alkali metal catalyzed alkylation reaction is the fact that the alpha carbon of the said alkylbenzene anion can add to either carbon atom comprising the olefinic double bond, giving two alkylation products.

Moderation of reaction conditions has proven to be effective in eliminating multiple alkylations. However, inability to conveniently improve upon addition specificity has heretofore remained problematic.

The presence of isomers due to non-specific addition of the alkylbenzene to the olefinic double bond has commercial consequences. In particular, it can have a grave impact on the overall rate of production of isobutyl benzene. For example, with the current method of producing isobutyl benzene (IBB), large amounts of normal-butyl benzene (NBB) are formed. As the boiling point of IBB (171° C.) is similar to the boiling point of NBB (183° C.), distillation to high purity is greatly complicated due to the necessity of removing a byproduct with a similar boiling point. In fact, the time required to distill off enough NBB to give an IBB product of sufficient purity for the required applications can cause purification to be the rate-limiting step in the production of IBB.

In addition to isomer formation, another problem with present processes is that the alkali metal catalysts utilized in the alkylation reaction seem to exacerbate the formation of insoluble tarry byproducts. Analysis of this byproduct indicates that it is comprised of high molecular weight molecules, likely the result of an alkali metal catalyzed polymerization reaction.

Other byproducts are formed as well. These are generally soluble in the reaction mixture, and their presence may cause the reaction mixture to have a darkened color.

The formation of tars and other byproducts has serious commercial consequences, as illustrated in the large-scale production of IBB. A current commercial method for the production of IBB is carried out as a batch process using a sodium/potassium alloy. The catalyst composition is prepared in situ by charging to the reactor toluene, small amounts of tall oil and water, and an amount of $NaK_2$ such that the mole ratio of $NaK_2$ to toluene is about 0.024. The temperature is raised to around 190° C. After about 15 minutes, propylene is fed to a reactor pressure of about 350 psig, and a $NaK_2$ to propylene mole ratio of about 0.028. After roughly 4–6 hours, the reaction mixture is cooled to about 50° C., and the reaction mixture is drained, and IBB is separated out. The process can be reiterated for successive batch production of IBB. Constant mechanical agitation is employed during the reaction in order to keep the catalyst and associated catalytic species emulsified; emulsification greatly increases the surface area on which benzyl potassium, the catalytically active complex in the alkylation reaction discussed above, can be formed, thus giving an enhanced reaction rate. It has been theorized that benzyl potassium coats each droplet of alloy, and that the alkylation occurs at the surface of the droplets. As the reaction proceeds, it is surmised that tar formed at the surface of a catalyst droplet accretes on the droplet, eventually encasing it. As the melting point of the tar is too high to be safely reached by the reactor, the accumulated tars inactivate large amounts of catalyst with each reaction run, making it necessary to recharge the reactor with catalyst in order to keep the reaction rate high. In addition, tar formation can shrink the reactor volume available for formation of product, giving diminishing yields of IBB at constant energy input. Also, frequent tar plugs in reactor lines often force a complete reactor cleaning, a drastic action which results in a waste of reactants and catalyst. Tar removal is complicated by the alkali metal core of each tar granule. Known methods must be conducted with extraordinary care, as the risk of uncontrolled reaction can be high; explosions are not unknown.

The formation of isomers, tars, and other byproducts has even further commercial consequences: a negative impact on catalyst and reactant utilization. Tar encased alkali metal has a greatly reduced ability to catalyze the formation of the alkylation product desired, and it is ultimately destroyed in the tar removal process. For example, a commercial process which produces 150,000 pounds of isobutyl benzene can be expected to lose over 0.25 million dollars due to unrecycled catalyst. Furthermore, reactants which could be used to form the desired product are discarded as byproducts. In the formation of isobutyl benzene, for instance, one mole of normal-butyl benzene is formed for every nine moles of isobutyl benzene. The formation of tars and other byproducts reduces reactant utilization to about fifty percent.

Schramm and Langlois (*Journal of the American chemical Society*, 1960, 82, 4912–4917) present a detailed study of the effect of different alkali metals on the yield of byproducts, particularly isomers due to non-selective addition at the olefinic double bond, at a wide range of temperatures. In trials in which potassium metal was used as a catalyst in the alkylation of toluene with propylene to produce IBB, Schramm, et al. observe a roughly temperature invariant value of nine for the alkylation product ratio of isobutyl benzene (IBB) to normal butyl benzene (NBB) over the temperature range of 107° C. to 204° C. In contrast, sodium catalyzes the alkylation in a temperature dependent manner, heavily favoring IBB at lower temperatures. An IBB to NBB ratio of about twelve is measured at 307° C., monotonically increasing to around twenty-four at 204° C. However, the Schramm and Langlois find that the data implies an activity for potassium that is at least an order of magnitude higher than that of sodium at all temperatures measured, specifically over the range of from 149° C. to 204° C. For example, at 149° C., sodium is expected to have an activity which is roughly one one-hundredth the activity of potassium. The activities of both metals increase monotonically with increasing temperature.

An illustration of the above findings can be seen in the current commercial process. Despite the fact that sodium catalysis gives an IBB to NBB ratio of roughly 23 at 190° C., Successive iterations of the process give product ratios, as defined above, of about nine, just as pure potassium gives in Schramm, et al. One might expect the sodium/potassium alloy to behave more like potassium due to sodium's relatively small activity at 190° C.

It would be of great importance if a way could be found of producing desired alkylbenzenes with greater selectivity and without formation of tars and other byproducts. If such could be accomplished while enabling recycle of catalyst residues from run to run, the state of the art would be vastly improved.

SUMMARY OF INVENTION

This invention provides novel, highly efficient process technology for the production of alkylbenzenes which makes possible the achievement of the foregoing advantages.

As the presence of tarry byproducts is a major impediment to optimum efficiency in the commercial preparation of IBB, it is desirable to reduce or eliminate their formation. A reduction in temperature has been associated with a decline in tar production in alkali metal catalyzed alkylation reactions (Schramm, et al.), but this is accompanied by a lower IBB production rate. In light of the observation that tar formation is likely catalyzed by the alkali metal, an increase in catalyst concentration in order to counter a reduced IBB production rate may seem counterproductive. The increase in tar formation would in all likelihood decrease reactant utilization to less than the fifty percent observed in the present commercial process. In addition, the projected increase in tar formation rate would be expected to inactivate catalyst at an even greater rate.

Surprisingly, when pursuant to this invention, alkylation is carried out at a lower temperature and a mixed sodium-potassium catalyst is used at a higher concentration than used heretofore, the amount of insoluble tars is visually undetectable, and the presence of colored soluble byproducts is dramatically reduced. In addition, the reaction rate is maintained at a level comparable with the present commercial process.

Thus, in accordance with this invention, there is provided in one of its embodiments a process which comprises:
A) forming a reaction mixture from components comprising (i) an alkene of greater than two carbon atoms, (ii) an alkylbenzene having at least one hydrogen atom on the alphacarbon atom of the alkyl group, and (iii) an alkali metal alkylation catalyst composition comprising sodium atoms, potassium atoms, and an alkylbenzene, the ratio of moles of potassium to moles of alkylbenzene being in the range of about 0.01 to about 0.30 moles of potassium per mole of alkylbenzene, and the atom ratio of sodium to potassium being in the range of about 0.1 to about 10.0 atoms of sodium per atom of potassium, and
B) maintaining said reaction mixture at one or more temperatures in the range of about 110° C. to about 180° C., at which the alkylbenzene thereof is alkylated on said alpha carbon atom to produce a reaction mass comprising (i) a longer chain alkylbenzene, and (ii) catalyst residue comprising sodium and potassium atoms, and removing at least a portion of said longer chain alkylbenzene from said reaction mass.

In conducting the process of this invention, it is possible to employ (i) fresh (i.e. virgin alkali metal alkylation catalyst composition), or (ii) a residual alkali metal alkylation catalyst composition from a prior run, or (iii) a combination of (i) and (ii). Another highly advantageous feature of this invention is that the residual catalyst composition is readily obtained from the reaction mass of a prior run conducted pursuant to this invention simply by allowing the reaction mass to stand long enough for a heavy layer comprised of catalyst residues to settle and thereafter to decant off the supernatant liquid alkylation product. All or a portion of the heavy catalyst residue can be used as a "heel" of residual catalyst in an ensuing run. Such processing was not possible in successive runs when conducting the current commercial method because of excessive tar formation.

Another beneficial feature of this invention is realized when utilizing in the alkylation reaction an asymmetrical alkene having at least one hydrogen atom on each carbon atom of the double bond. In such cases, the formation of two different isomeric products is possible depending upon the manner in which the alkylbenzene adds to such asymmetrical alkene. For example, reaction of 1-pentene with toluene tends to yield mixtures of 2-methylpentylbenzene and n-hexylbenzene. The former product involves addition to the more internal doubly-bonded carbon atom of the alkene, whereas the latter product involves addition to the less internal doubly-bonded carbon atom of the alkene. Surprisingly, when conducting a series of runs pursuant to this invention, especially when these runs are conducted in the same reactor, the ratio of the two isomeric products tends to progressively favor formation of the product involving addition to the more internal doubly-bonded carbon atom. It has been found, for example, that in a series of alkylations pursuant to this invention involving toluene and propylene, the ratios of isobutylbenzene to n-butylbenzene tends to increase as the number of alkylation runs increases, starting with a ratio of about 9:1 and reaching as high as about 20:1, or even higher, in later runs.

The trend of increasing product ratio in succeeding runs is not only highly beneficial, but is unforeseeable in light of the findings reported by Schramm, et al. to the effect that the product ratios and metal activities are affected in opposite ways by a drop in temperature. In particular, from Schramm, et al. sodium expected to exhibit an almost negligible activity at around 150° C. Thus, the conventional product ratio of 9:1 associated with potassium could be expected for every reaction in a series. However, the present invention makes possible product ratios which reach as high as 20:1, or more.

The above and other embodiments and features of this invention will be apparent from the ensuing description and appended claims.

Formation of Alkali Metal Alkylation Catalyst Compositions

The alkylbenzenes used in forming the catalyst include, for example, toluene, o-xylene, m-xylene, p-xylene, 1-ethyl-2-methylbenzene, 1-ethyl-3-methylbenzene, 1,3-diethylbenzene, 1,2-diethylbenzene; 1,2,3-trimethylbenzene, 1,2,4-trimethylbenzene, 1,4-diethyl-3-methylbenzene, 3-isopropyl-1-methylbenzene, 4-isopropyl-1-methylbenzene, 4-isopropyl-1,2-dimethylbenzene,1,2- diethyl-4-isopropylbenzene, 2,4-diisopropyl-1-methylbenzene, 1,3,5-triisopropylbenzene, 3-isopropyl-1-methyl-5-tert-butylbenzene, 1,3-diisopropyl-5-tert-butylbenzene, 1,3-diisopropyl-5-tert-butylbenzene, 1-isopropyl-3,5-di-tert-butylbenzene, 2-nitro-3-methyltoluene, 3-nitro-4-methyltoluene, 3-nitro-4-ethyltoluene, 1-methoxy-2,3-diethylbenzene, 1-ethoxy-3,4-diethylbenzene, 1-methylthio-3-isopropyl-2-methylbenzene, 1-phenoxy-2-isopropyl-3-tert-butylbenzene, 1-methoxy-3-isopropyl-2-methylbenzene, 1-ethylthio-2-isopropyl-3-tert-butylbenzene, 1-nitro-3-isopropyl-2-methyl-5-tert-butylbenzene, and analogous alkylbenzenes, preferably substituted with electron donating functional groups in one or more positions in such a way as to permit or facilitate the formation of a net negative charge on a carbon atom which is alpha to the ring. Preferred is an alkyl-substituted toluene. Most preferred is toluene.

The original or fresh catalyst compositions can be formed (i.e., produced) from (a) sodium metal and/or organosodium compound, and (b) potassium metal and/or organopotassium compound as raw materials, in a ratio of about 0.10 to about 10.00 atoms of sodium per atom of potassium. If an organosodium and/or organopotassium compound is used as a raw material in forming the alkali metal alkylation catalyst composition, such organosodium and/or organopotassium compound can be preformed or it can be produced in situ from the alkali metal and an appropriate reactant such as an alkene, an alkylbenzene having at least one hydrogen atom alpha to the ring, a nitroalkene having at least one hydrogen atom on the carbon atom which is alpha to a double bond, a nitroalkane having at least one acidic hydrogen atom, an alkoxyalkane having at least one acidic hydrogen atom, an alkylthioalkane having at least one acidic hydrogen atom, a nitroalkylbenzene having at least one hydrogen atom alpha to the ring, an alkoxyalkylbenzene having at least one hydrogen atom alpha to the ring, and any analogous functionally-substituted hydrocarbon having an acidic hydrogen atom.

When both metals are used in forming the initial or fresh catalytic ion pair, they can be used as individual free metals or as a mixture or alloy of sodium and potassium. An alloy with a ratio of sodium to potassium which falls in the range of about 0.1 to about 10.0 atoms of sodium per atom of potassium is preferred. The alloy with a ratio of sodium to potassium of about 0.5 atom of sodium per atom of potassium ($NaK_2$) is most preferred.

When the catalytic ion pair is produced in whole or in part from organosodium compound(s) and/or organopotassium compound(s), various organocompounds of these metals can be used. For example they can be alkyl, alkenyl, cycloalkyl, cycloalkenyl, aryl, or aralkyl sodium or potassium compounds such as pentyl sodium, hexenyl sodium, phenyl sodium, naphthyl sodium, benzyl sodium, butyl potassium, propenyl potassium, phenyl potassium, cyclohexenyl potassium, 4-methylbenzyl potassium, and analogous compounds. Of the organosodium and organopotassium compounds used in forming the fresh catalyst, it is preferred to utilize a organosodium or organopotassium compound which facilitates or permits formation of a negative charge on the carbon atom with which the sodium or potassium is associated.

To form the initial or fresh alkali metal alkylation catalyst composition, a mixture is formed from (a) sodium metal and/or organosodium compound(s), (b) potassium metal and/or organopotassium compound(s), and (c) an alkylbenzene having at least one hydrogen atom on the alpha carbon atom of the alkyl group. The proportions of these components are such that (1) the atom ratio of sodium to potassium is from about 0.1 to about 10.00, and preferably from about 0.3 to about 0.7 atom of sodium per atom of potassium (irrespective of whether such atoms are in the form of free metal or as an organometal compound, or both), and (2) the ratio of moles of potassium (again, irrespective of whether the potassium is in the form of free metal or as an organometal compound, or both), per mole of the alkylbenzene is in the range of about 0.01 to about 0.30 mole of potassium per mole of alkylbenzene, and preferably in the range of about 0.03 to about 0.10 mole of potassium per mole of alkylbenzene. Particularly preferred is a ratio in the range of about 0.03 to about 0.05, (e.g., 0.045) mole of potassium per mole of alkylbenzene. The resultant mixture is heated to temperatures in the range of about 90° C. to about 240° C., and preferably in the range of about 140° C. to about 200° C., to form the fresh alkali metal alkylation catalyst composition. When forming the catalyst composition from sodium and potassium metals and toluene, the most preferred temperature is in the range of about 170 to about 190° C., e.g., 185° C.

Small amounts of water can be used to enhance the activity of the alkali metal. The added water is surmised to react with the alkali metal to form alkali metal oxides which improve the activity of the alkali metal in forming the catalyst composition. Preferred is a mole ratio of water to alkali metal in the range of about 0.00 to about 0.10. Most preferred is a ratio of about 0.04 to about 0.06. Added amounts of tall oil in the catalyst formation reaction and in the alkylation reaction have been observed to aid in the emulsification of the alkali metal catalyst composition. Preferred is a weight ratio of tall oil to total potassium in the catalyst composition in the range of about 0 to about 100. Most preferred is a ratio of about 1 to about 5.

The amount of time sufficient for catalyst ion pair formation can be in the range of about 0.0 hour to about 10.0 hours. Preferred is a time in the range of from about 0.2 hour to about 1.0 hour. Most preferred is a time of about 0.5 hour.

Mechanical agitation can be beneficial to the formation of the catalyst ion pair. Preferred is a rotary stirrer.

Typically the first alkylation run of a series of alkylation runs is conducted using a fresh alkali metal alkylation catalyst. Subsequent runs, which preferably are conducted in the same reactor, can be run using a heel containing catalyst residue from a prior alkylation run conducted pursuant to this invention and from which at least a portion of the longer chain alkylbenzene has been removed. Preferably in most, if not all, alkylation runs of a series, the reaction mixture contains both a portion of fresh alkali metal alkylation catalyst and a heel containing residual catalyst residue from a prior alkylation run. In other words, it is preferred to employ fresh catalyst as needed or as desired along with a heel containing residual catalyst from a prior run.

Alkylation I

The first alkylation reaction is generally carried out following the catalyst ion pair formation reaction. The alkylation reaction can be, and preferably is, conducted in the same reactor in which the above alkali metal alkylation catalyst composition was formed, and in such case the catalyst for the alkylation reaction is already present in the reactor. However, it is also possible to conduct the first alkylation reaction in a separate reactor into which is charged the catalyst ion pair prepared as above, and the reactants. The alkylbenzenes which are utilized in the alkylation reaction span a wide range which comprises the alkylbenzenes referred to above in connection with formation of the alkali metal alkylation catalyst composition. Preferred is an alkyl-substituted toluene. Most preferred is toluene.

The alkenes which are suitable for use in the alkylation reaction include, but are not limited to propylene, 1-butene, 2-butene, 3-methyl-1-butene, 2-methyl-1-propene, 1-pentene, 2-pentene, 1-hexene, cyclohexene, 1-octene, 1-decene, 4-tetradecene, and other analogous olefinic hydrocarbons, as well as olefins which are substituted with suitable functionality in such a way as to permit or facilitate bond formation between 1) an alkylbenzene carbon atom which is alpha to the benzene ring on which a negative charge or a part thereof is more or less localized, and 2) either of the two carbon atoms between which existed a double bond prior to alkylation. An alkene hydrocarbon of less than five carbon atoms is preferred. Most preferred is propylene.

Typically the mole ratio of alkene to the alkylbenzene reactant in the reaction mixture is in the range of about 0.01 to about 10.00 moles of the alkene per mole of the alkylbenzene. Preferably, this ratio is in the range of about 0.8 to about 0.9 moles of alkene per mole of the alkylbenzene reactant.

With gaseous alkene reactants, the pressure maintained within the reactor in the first alkylation should be in the range of about 100 psig to about 800 psig. Most preferred when using propylene or a butylene is a pressure in the range of about 250 psig to about 350 psig. Liquid alkenes can be reacted under subatmospheric, atmospheric or superatmospheric pressures.

A desirable mole ratio of 1) potassium in the alkali metal catalyst composition to 2) the alkylbenzene initially present in the reactor in the first alkylation reaction is typically in the range of about 0.01 to about 0.30 mole of potassium per mole of such alkylbenzene. Preferred is a ratio in the range of about 0.03:1 to about 0.1:1. Most preferred is a ratio in the range of about 0.03:1 to about 0.05:1, e.g., about 0.045:1.

Successful suppression of byproducts may occur at a range of temperatures. Preferred is a temperature in the range of from about 100° C. to about 180° C. Most preferred is a temperature in the range of from about 130° C. to about 160° C.

The time during which the alkylation reaction mixture is maintained at reaction temperatures can be in the range of from about 1 hour to about 10 hours. Most preferred is a reaction period in the range of from about 4 hours to about 6 hours.

Separation of the desired product generally begins by allowing the residual catalytic material to settle in the reactor, followed by decanting the reactor of the remaining contents. It is preferable during such decanting to ensure that the reactor contents remain at a minimum temperature in the range of about 100° C. to about 180° C. in order to avoid the precipitation of byproducts. Most preferred is a temperature of about 120° C. Other means of separation comprising methods such as filtration or centrifugation may be used instead of/in addition to settling and decanting. Settling and decanting is preferred. The portion containing large amounts of product can then be stored or purified as desired.

Without desiring to be bound by theory, a mechanism by which the alkylation is theorized to take place is as follows. As a result of the catalyst ion pair formation reaction, the alkali metal exists in solution as a cation, having facilitated the formation of an anion at the alpha carbon atom of the alkylbenzene and/or alkene utilized in said reaction. In the alkylation step, the alkali metal cation enables the reaction by associating with the double bond of the alkene, partially delocalizing its electrons. The resulting complex is susceptible to nucleophilic attack by the said anion, giving two possible addition products which are chain-lengthened at the alpha carbon atom. The alkali metal next associates with the carbon atom which was previously involved in the double bond, but is not presently connected to the alpha carbon of the nucleophile. Subsequently, it is replaced by the acidic alpha hydrogen atom of another molecule in the reaction mixture, recreating an anion which may repeat the above process.

Alkylation II and Successive Alkylations

The alkylbenzenes which may be utilized in the second alkylation reaction comprise the alkylbenzenes which may be utilized in the preceding reactions. In most cases the alkylbenzene used will be the same as that used in the prior run. Preferred is an alkyl-substituted toluene. Most preferred is toluene.

The alkenes which may be utilized in the second reaction comprise the alkenes suitable for the first alkylation reaction. It is preferred, but not essential, to use the same alkene in successive runs. Preferred is an alkene of less than five carbons. Most preferred is propylene.

Typically, the mole ratio of the alkene reactant to the alkylbenzene reactant in the reaction mixture prior to alkylation II and successive alkylations is in the range of about 0.05 to about 10.00 moles of alkene per mole of the alkylbenzene. Preferably, this ratio is in the range of about 0.80 to about 0.90 moles of alkene per mole of the alkylbenzene reactant.

The mole ratio of potassium present in the reactor in this run to alkylbenzene which is present in the reactor in this run may be in the range of about 0.01 to about 0.30 mole of potassium per mole of alkylbenzene. Preferred is a ratio of about 0.03 to about 0.10 mole of potassium per mole of alkylbenzene. Most preferred is a ratio in the range of about 0.03 to about 0.05, e.g., 0.045.

The reaction mixture in the second and succeeding runs can be a heel containing all or a portion of the residual catalyst from a prior run, and from which at least a portion of the longer chain alkylbenzene product has been removed. Preferably, however the catalyst composition used is the combination of (1) fresh alkali metal alkylation catalyst composition prepared as described above, and (2) a heel from a prior alkylation reaction mass containing residual alkali metal-containing catalyst residues and from which reaction mass at least a portion of the longer chain alkylbenzene product has been removed.

Small amounts of water can be included in the reaction mixture to enhance the catalytic activity of the alkali metal alkylation catalyst composition. Preferred is a mole ratio of water to potassium in the range of about 0.0 to about 0.1. Most preferred is a ratio in the range of about 0.04 to about 0.06 mole of water per mole of potassium. Small amounts of tall oil can be added as well. Preferred is a weight ratio of tall oil to potassium in the range of about 0 to about 100 parts of tall oil per part of potassium. Most preferred is a ratio of about 1 to about 5 parts by weight of tall oil per part by weight of potassium.

The ratio of potassium charged to the reactor to alkene charged to the reactor may be in the range of about 0.0 to about 0.03 mole of potassium per mole of alkene. Preferred is a ratio of from about 0.00 to about 0.01 mole of potassium per mole of alkene. Most preferred is a ratio of about 0.007.

A desirable ratio of sodium to potassium in the reaction mixture (whether from recycled catalyst residue in a heel from a prior run, or from a combination of recycled catalyst residue in a heel from a prior run plus fresh catalyst) is within the range of 0.1 to 10.0 atoms of sodium per atom of potassium. Preferable is a ratio of about 0.3 to about 0.7 atom of sodium per atom of potassium. Most preferable is a ratio of about 0.5.

With gaseous alkene reactants, the pressure maintained within the reactor in these alkylation runs should be in the range of about 100 psig to about 800 psig. Most preferred when using propylene or a butylene is a pressure in the range of about 250 psig to about 350 psig. Liquid alkenes can be reacted under subatmospheric, atmospheric or superatmospheric pressures.

It is desirable that the temperature at which the reaction is conducted be in the range of from about 100° C. to about 180° C. Preferred is a range of from about 130° C. to about 160° C. Most preferred is a temperature in the range of about 145 to about 155° C., e.g., 150° C.

The time over which the reaction is conducted may be in the range of about 1 hours to about 10 hours. Preferred is a range of from about 4 hours to about 6 hours. Most preferred is a time of about 5 hours.

Separation of desired products may be accomplished as in the first alkylation run. The alkylation process set forth above may be repeated many times in succession as desired. The mechanism discussed in the previous section is relevant in this section as well.

The practice of this invention is illustrated by the following non-limiting example.

EXAMPLE

Preparation of Isobutylbenzene

Charge to an empty reactor at ambient temperature, toluene (13,140 pounds), and tall oil (2 pounds), to form a mixture containing 250 ppm of water. Charge $NaK_2$ (320 pounds) to the reactor and heat the contents to 190° C. for 0.5 hour, using mechanical agitation to maintain $NaK_2$ as an emulsion. Cool the reactor to 150° C., and charge propylene (5130 pounds) to a pressure of 300 psig. Maintain the reactor temperature at 150° C. for 90 minutes with continuous mechanical agitation. Cool the reactor to 120° C., and vent off propylene to a pressure of 20 psig. Turn off the agitator and allow the catalyst phase to settle, and decant off the remainder of the superposed reaction mass, so that the reactor contains the residual catalyst composition. Restart the agitator, and charge to the reactor a mixture of toluene (12,120 pounds) which has been preheated to 120° C., tall oil (1 pound), and $NaK_2$ (40 pounds), which mixture has a water content of 130 ppm. Raise the reactor temperature to 150° C., and charge propylene (4700 pounds) to a pressure of 300 psig. Agitate the reaction mixture for 90 minutes at about 150° C. Cool the reactor to 120° C., and vent off propylene to a pressure of 20 psig. Turn off the agitation, allow the catalyst phase to settle, and decant off the remainder of the reaction mass which disposed above the settled catalyst. The alkylation is then repeated successively 12 more times using the combination of fresh catalyst ($NaK_2$) and a heel of the catalyst residue from the immediately preceding run. The amounts of materials charged to the reactor in each run and the results achieved in each such run are summarized in the following table.

TABLE

| Run # | Water (ppm) | Tall Oil (Lbs) | Toluene (Lbs) | Propylene (Lbs) | $NaK_2$ (Lbs) | IBB (Lbs) | IBB (wt %) | NBB (wt %) | IBB/NBB mole/mole |
|---|---|---|---|---|---|---|---|---|---|
| 1 | 250 | 2 | 13140 | 5130 | 320 | 7961 | 56.1 | 6.2 | 9.0 |
| 2 | 130 | 1 | 12120 | 4700 | 40 | 8723 | 55.9 | 6.2 | 9.0 |
| 3 | 130 | 1 | 12040 | 4700 | 40 | 8942 | 57.3 | 5.9 | 9.7 |
| 4 | 130 | 1 | 12040 | 4700 | 40 | 9113 | 58.4 | 5.2 | 11.3 |
| 5 | 170 | 1 | 12040 | 4700 | 40 | 8957 | 57.4 | 4.9 | 11.7 |
| 6 | 170 | 1 | 12040 | 4730 | 40 | 9372 | 60.1 | 4.7 | 12.8 |
| 7 | 170 | 1 | 12040 | 4200 | 40 | 9175 | 54.5 | 4.5 | 12.1 |
| 8 | 270 | 1 | 12040 | 4700 | 40 | 9601 | 57.8 | 4.9 | 11.8 |
| 9 | 270 | 1 | 12040 | 4700 | 40 | 9664 | 58.2 | 4.8 | 12.1 |
| 10 | 270 | 1 | 12040 | 4700 | 40 | 9651 | 58.1 | 4.7 | 12.5 |
| 11 | — | 1 | 12040 | 4700 | 40 | 9697 | 58.4 | 4.5 | 13.1 |
| 12 | — | 1 | 12040 | 4700 | 40 | 9505 | 57.2 | 4.6 | 12.5 |
| 13 | — | 1 | 12040 | 4700 | 80 | 9465 | 57.0 | 4.6 | 12.4 |
| 14 | — | 1 | 12040 | 4700 | 50 | 9465 | 57.0 | 4.4 | 13.0 |

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", is, etc.), the reference is to the substance, component or ingredient as it existed at the time just before it was first contacted, blended or mixed with one or more other substances, components and/or ingredients in accordance with the present disclosure. Without limiting the generality of the foregoing, as an illustrative example, where a claim specifies that a catalyst is a palladium compound in combination with a tertiary phosphine ligand, this phraseology refers to the makeup of the individual substances before they are combined and/or mixed separately or concurrently with one or more other materials, and in addition, at the time the catalyst is actually performing its catalytic function it need not have its original makeup—instead whatever transformations, if any, that occur in situ as the catalytic reaction is conducted is what the claim is intended to cover. Thus the fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

Each and every patent or publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. An alkylation process which comprises:
   A) contacting in a reactor components comprising (I) an alkene of greater than two carbon atoms, (II) an alkylbenzene having at least one hydrogen atom on the alpha-carbon atom of the alkyl group, (III) a sodium and potassium alkylation catalyst composition comprising:
      (a) fresh sodium and potassium alkylation catalyst composition, either preformed or formed in situ, by a process which comprises heating a mixture formed from components comprising (i) an alkylbenzene having at least one hydrogen atom on the alpha carbon atom of the alkyl group, and (ii) a mixture of (1) sodium metal and/or organosodium compound, and (2) potassium metal and/or organopotassium compound in a ratio of about 0.1 to about 10.0 atoms of sodium per atom of potassium, as well as a ratio of about 0.01 to about 0.30 mole of potassium per mole of said alkylbenzene of (i), at one or more temperatures at which a fresh sodium and potassium alkylation catalyst composition is formed; or
      (b) a mixture of fresh catalyst composition formed as in (a) and residual sodium and potassium catalyst from a prior alkylation reaction conducted in accordance with Step B) hereinafter;
      and (IV) water, in amounts such that a reaction mixture is formed in which:
      the ratio of potassium to alkylbenzene reactant is in the range of about 0.01 to about 0.30 mole of potassium per mole of alkylbenzene reactant,
      the ratio of sodium to potassium is in the range of about 0.1 to about 10.0 atoms of sodium per atom of potassium, and
      the ratio of water to potassium is in the range of up to about 0.1 mole of water per mole of potassium; and
   B) maintaining the reaction mixture of A) at one or more temperatures in the range of about 100° C. to about 180° C. at which alkylation occurs and a reaction mass comprising (i) a longer chain alkylbenzene product, and (ii) residual sodium and potassium catalyst is produced, and removing at least a portion of the longer chain alkylbenzene product from said reaction mass.

2. A process of claim 1 wherein the alkene of (I) in A) is propylene, and the alkylbenzene of (II) in A) is toluene.

3. A process of claim 1 wherein the sodium and potassium alkylation catalyst composition of (III) in A) has an atom ratio of sodium to potassium in the range of about 0.3 to about 0.7 atom of sodium per atom of potassium.

4. A process of claim 1 wherein the temperature in B) is in the range of about 130° C. to about 160° C.

5. A process of claim 1 wherein the ratio of potassium to the alkylbenzene reactant present in the reaction mixture of A) is in the range of about 0.03 to about 0.10 mole of potassium per mole of alkylbenzene reactant present in the reaction mixture of A).

6. A process of claim 1 wherein the sodium and potassium alkylation catalyst composition of (III) in A has an atom ratio of about 0.5 atom of sodium per atom of potassium.

7. A process of claim 1 wherein the temperature in B) is about 145 to about 155° C.

8. A process of claim 1 wherein the alkylbenzene of (II) in A) is toluene, wherein the alkene of (I) in A) is propylene, wherein the temperature in B) is in the range of about 145 to about 155° C., wherein the ratio of the sodium and potassium alkylation catalyst composition of (III) in A) to the toluene present in the reaction mixture of A) is in the range of about 0.03 to about 0.05 mole of potassium per mole of the toluene present in the reaction mixture, and wherein the reaction mass contains no visibly perceptible amount of tar.

9. A process of claim 1 wherein said sodium and potassium metal alkylation catalyst composition of (III) in A) is a fresh catalyst composition formed as in (a) of claim 1.

10. A process of claim 1 wherein said sodium and potassium alkylation catalyst composition of (III) in A) is residual sodium and potassium catalyst from a prior alkylation reaction conducted in accordance with Step B).

11. A process of claim 1 wherein said sodium and potassium alkylation catalyst composition of (III) in A) comprises a mixture of fresh catalyst composition formed as in (a) of claim 1 and residual sodium and potassium catalyst from a prior alkylation reaction conducted in accordance with Step B).

12. A process of claim 9, 10, or 11 wherein the alkene of (I) in A) is propylene, and the alkylbenzene of (II) in A) and of (i) in (a) is toluene.

13. A process of claim 9, 10, or 11 wherein the sodium and potassium alkylation catalyst composition of (III) in A) has an atom ratio of sodium to potassium in the range of about 0.3 to about 0.7 atom of sodium per atom of potassium.

14. A process of claim 9, 10, or 11 wherein the temperature in B) is in the range of about 130° C. to about 160° C.

15. A process of claim 9, 10, or 11 wherein the ratio of potassium to alkylbenzene reactant present in the reaction mixture in A) is in the range of about 0.03 to about 0.10 mole of potassium per mole of said alkylbenzene reactant.

16. A process of claim 9, 10, or 11 wherein the sodium and potassium alkylation catalyst composition of (III) in A) has an atom ratio of about 0.5 atom of sodium per atom of potassium.

17. A process of claim 9, 10, or 11 wherein the temperature in B) is in the range of about 145 to about 155° C.

18. A process of claim 9 or 11 wherein the alkylbenzene used in forming said fresh catalyst is toluene.

19. An alkylation process which comprises:
   A) contacting in a reactor components comprising (I) an asymmetrical alkene having at least one hydrogen atom on each carbon atom of the double bond, (II) an alkylbenzene having at least one hydrogen atom on the alpha-carbon atom of the alkyl group, (III) a sodium and potassium alkylation catalyst composition comprising:
      (a) fresh sodium and potassium alkylation catalyst composition, either preformed or formed in situ, by a process which comprises heating a mixture formed from components comprising (i) an alkylbenzene having at least one hydrogen atom on the alpha carbon atom of the alkyl group, and (ii) a mixture of (1) sodium metal and/or organosodium compound, and (2) potassium metal and/or organopotassium compound in a ratio of about 0.1 to about 10.0 atoms of sodium per atom of potassium, as well as a ratio of about 0.01 to about 0.30 mole of potassium per mole of said alkylbenzene of (i), at one or more temperatures at which a fresh sodium and potassium alkylation catalyst composition is formed; or (b) a mixture of fresh catalyst composition formed as in (a) and residual sodium and potassium catalyst from a prior alkylation reaction conducted in accordance with Step B) hereinafter;

and (IV) water, in amounts such that a reaction mixture is formed in which:

the ratio of potassium to alkylbenzene reactant is in the range of about 0.01 to about 0.30 mole of potassium per mole of alkylbenzene reactant, the ratio of sodium to potassium is in the range of about 0.1 to about 10.0 atoms of sodium per atom of potassium, and the ratio of water to potassium is in the range of up to about 0.1 mole of water per mole of potassium; and B) maintaining the reaction mixture of A) at one or more temperatures in the range of about 100° C. to about 180° C. at which alkylation occurs and a reaction mass comprising (i) a longer chain alkylbenzene product, and (ii) residual sodium and potassium catalyst is produced, and removing at least a portion of the longer chain alkylbenzene product from said reaction mass;

C) forming from another group of components, another reaction mixture in which alkylation is to take place, this group of components comprising (I) the same kind of asymmetrical alkene having at least one hydrogen atom on each carbon atom of the double bond, as used in A), (II) the same kind of alkylbenzene having at least one hydrogen atom on the alpha-carbon atom of the alkyl group, as used in A), (III) residual sodium and potassium catalyst from a prior alkylation reaction conducted in accordance with Step B), (IV) water, and (V) optionally fresh sodium and potassium alkylation catalyst composition formed as in (a) hereinabove, such that in this latter reaction mixture:

the ratio of potassium to alkylbenzene reactant is in the range of about 0.01 to about 0.30 mole of potassium per mole of alkylbenzene reactant, the ratio of sodium to potassium is in the range of about 0.1 to about 10.0 atoms of sodium per atom of potassium, and the ratio of water to potassium is in the range of up to about 0.1 mole of water per mole of potassium; and D) maintaining the reaction mixture of C) at one or more temperatures in the range of about 100° C. to about 180° C. at which alkylation occurs and a reaction mass comprising (i) a longer chain alkylbenzene product, and (ii) residual sodium and potassium catalyst is produced, and removing at least a portion of the longer chain alkylbenzene product from this reaction mass; and E) repeating Steps C) and D) successively such that in at least a plurality of such successive alkylation reactions the ratio of (i) the longer chain alkylbenzene isomer formed via addition to the more internal doubly-bonded carbon atom to (ii) the longer chain alkylbenzene isomer formed via addition to the less internal doubly-bonded carbon atom, is greater than in the alkylation reaction of B).

20. A process of claim 19 wherein the sodium and potassium alkylation catalyst composition used in A) consists essentially of fresh catalyst composition, either preformed or formed in situ, by a process which comprises heating a mixture formed from components comprising (i) toluene and (ii) $NaK_2$ and/or a mixture of (1) sodium metal and (2) potassium metal in a ratio of about 0.5 atom of sodium per atom of potassium, as well as a ratio of about 0.01 to about 0.30 mole of potassium per mole of said toluene of (i), at one or more temperatures at which a fresh sodium and potassium alkylation catalyst composition is formed, wherein the alkene of (I) in A) is propylene, wherein the alkylbenzene of (II) in A) is toluene, wherein Steps C) and D) of said process are repeated successively in the same reactor, and wherein when a consecutive group of at least 10 such alkylation process runs is conducted under essentially the same conditions, the ratio of isobutylbenzene to n-butylbenzene produced is greater in the tenth such run than in the first such run.

21. A process of claim 19 wherein said alkylation process of Steps C) and D) is repeated successively in the same reactor, and wherein when a consecutive group of at least 10 said alkylation process runs is conducted under essentially the same conditions, the ratio of (i) the longer chain alkylbenzene isomer formed via addition to the more internal doubly-bonded carbon atom to (ii) the longer chain alkylbenzene isomer formed via addition to the less internal doubly-bonded carbon atom, is greater in the tenth such alkylation process run than in the first such alkylation process run.

22. A process of claim 19 wherein the alkene of (I) in A) is propylene, wherein the alkylbenzene of (II) in A) is toluene, wherein said alkylation process of Steps C) and D) is repeated successively in the same reactor, and wherein when a consecutive group of at least 10 such alkylation process runs is conducted under essentially the same conditions the ratio of isobutylbenzene to n-butylbenzene produced is greater in the tenth such run than in the first such run.

23. A process of claim 19 wherein Steps C) and D) of said alkylation process are repeated successively in the same reactor, and wherein when a consecutive group of at least 5 such alkylation process runs is conducted under essentially the same conditions, the reaction mass contains no visibly perceptible amount of tar.

24. A process of claim 23 wherein the alkene of (I) in A) is propylene and the alkylbenzene reactant of (II) in A) is toluene.

25. A process of claim 19 wherein Steps C) and D) of said alkylation process are repeated successively in the same reactor, wherein in the first such alkylation process run the catalyst of (III) in A) is a fresh catalyst composition formed as in (a) of claim 19, wherein in each of 4 successive alkylation process runs the catalyst is a mixture in accordance with (b) of claim 19, and wherein in such consecutive group of 5 such alkylation process runs conducted under essentially the same conditions, the reaction mass contains no visibly perceptible amount of tar.

26. A process of claim 25 wherein the alkene of (I) in A) is propylene and the alkylbenzene reactant of (II) in A) is toluene.

27. A process which comprises:

A) forming a fresh alkali metal catalyst composition by a process which comprises heating a mixture formed from components comprising (i) toluene and (ii) sodium-potassium alloy of the formula $NaK_2$, at one or more temperatures at which a fresh alkali metal catalyst composition is formed;

B) forming a reaction mixture from components comprising (i) propylene, (ii) toluene, (iii) fresh alkali metal catalyst composition from A), and water in amounts such that the ratio of potassium to toluene is in the range of about 0.03 to about 0.10 mole of potassium per mole of toluene present in the reaction mixture, and the ratio of water to potassium is in the range of up to about 0.1 mole of water per mole of potassium;

C) maintaining said reaction mixture at one or more temperatures in the range of about 100° C. to about 180° C. at which is formed a reaction mass comprising (i) isobutylbenzene, and (ii) catalyst residue comprising sodium and potassium atoms, and removing at least a portion of the isobutylbenzene from said reaction mass; and D) forming a mixture from components comprising (i) propylene, (ii) toluene, (iii) fresh alkali metal catalyst composition from A), (iv) catalyst residue formed as in C), and (v) water, in amounts such that the ratio of potassium to toluene is in the range of about 0.03 to about 0.10 mole of potassium per mole of toluene present in the mixture of D), and the ratio of water to potassium is in the range of up to about 0.1 mole of water per mole of potassium; and E) maintaining said mixture of D) at one or more temperatures in the range of about 100° C. to about 180° C. at which is formed a reaction mass comprising (i) isobutylbenzene, and (ii) catalyst residue comprising sodium and potassium atoms, and removing at least a portion of the isobutylbenzene from said last-mentioned reaction mass.

28. A process of claim 19 or 27 wherein the temperature in C) is in the range of from about 130° C. to about 160° C., and wherein the temperature in E) is in the range of from about 130° C. to about 160° C.

29. A process of claim 27 or 19 wherein the temperature in C) is in the range of from about 130° C. to about 160° C., and wherein the temperature in E) is in the range of from about 145° C. to about 155° C.

30. A process of claim 27 or 19 wherein D) and E) are conducted in the same reactor as B) and C).

31. A process of claim 27 or 19 wherein A), B), C), D), and E) are conducted in the same reactor.

* * * * *